United States Patent [19]

Nardi et al.

[11] 4,115,390

[45] Sep. 19, 1978

[54] METHOD FOR THE PREPARATION OF 1-ALKYL PYRIDINIUM CHLORIDES

[76] Inventors: John C. Nardi, 3398 Tyler Dr., Brunswick, Ohio 44212; Charles L. Hussey, Quarters 6402H, USAF Academy, Colo. 80840; Lowell A. King, 460 Winters Cir. N., Colorado Springs, Colo. 80919; Ronald A. Carpio, 21 N. Garland Ave., Colorado Springs, Colo. 80909

[21] Appl. No.: 826,222

[22] Filed: Aug. 19, 1977

[51] Int. Cl.$^2$ .................................. C07D 213/04
[52] U.S. Cl. ..................... 260/290 HL; 260/290 R
[58] Field of Search .................... 260/290 HL, 290 R

*Primary Examiner*—Alan L. Rotman
*Attorney, Agent, or Firm*—Joseph E. Rusz; William J. O'Brien

[57] ABSTRACT

A method for preparing alkyl pyridinium chlorides by effecting a direct reaction between the corresponding alkyl chloride and pyridine.

5 Claims, No Drawings

METHOD FOR THE PREPARATION OF 1-ALKYL PYRIDINIUM CHLORIDES

STATEMENT OF GOVERNMENT INTEREST

The invention described herein may be manufactured and used by or for the Government for governmental purposes without the payment of any royalty thereon.

BACKGROUND OF THE INVENTION

This invention relates to a method for preparing alkyl pyridinium chlorides. More particularly, this invention concerns itself with a simplified process that permits the convenient synthesis of alkyl pyridinium chlorides in which the alkyl moiety is selected from the group consisting of 1-methyl, 1-ethyl, 1-propyl and 1-butyl radicals.

Recent interest in the utilization of low temperature, thermally activated batteries for various aerospace and military applications has in turn, generated considerable interest in developing new products for use as component parts in thermal battery systems. For example, it has been recently determined that fused salt mixtures of aluminum chloride and alkyl pyridinium chloride form low melting eutectics making them especially suitable for use as the electrolytic medium of a thermal battery. The practical synthesis of these chloride salts, therefore, is a matter of some importance.

Various methods for synthesizing alkyl pyridinium chloride have been reported. However, very little experimental detail has been given in prior investigations and virtually no characterization of the compounds has been made. Furthermore, yields of the salts produced by known methods have been low or unreported.

With this invention, however, it has been found that the problem of low yield encountered with prior art methods of synthesis has been overcome by a simplified process which permits the direct reaction of pyridine and an appropriate alkyl halide.

Accordingly, the primary object of this invention is to provide a convenient and simplified method for preparing alkyl pyridinium chlorides in relatively high yield.

Another object of this invention is to provide a convenient process for the synthesis of alkyl pyridinium chlorides through the direct reaction of pyridine and the corresponding alkyl halide.

The above and still other objects and advantages of the present invention will become more readily apparent upon consideration of the following detailed description thereof.

DESCRIPTION OF THE PREFERRED EMBODIMENTS

In accordance with this invention, it has been found that the above described objects can be accomplished by effecting a reaction between pyridine and an alkyl halide selected from the group consisting of chloromethane, chloroethane, 1-chloropropane and 1-chlorobutane.

Recent investigations in the utilization of thermally activated batteries and the development of component parts for use therewith have provided information which shows that mixtures of aluminum chloride and alkyl pyridinium chloride form low melting eutectic mixtures. The mixtures are especially suitable for use as electrolytes in thermal batteries. These fused salt mixtures possess a large electrochemical window which permits their use in batteries. The practical synthesis of the alkyl pyridinium chlorides in high yield, therefore, becomes an important objective for those interested in developing thermal battery components, such as the electrolytic medium referred to above.

The objective referred to above was achieved by effecting a reaction between pyridine and an appropriate alkyl chloride in order to synthesize the corresponding alkyl pyridinium chloride. The reaction components are mixed and a direct reaction therebetween is accomplished under mild reaction conditions to give good yields of the resultant reaction product.

In order to further illustrate to those skilled in the art the best mode of operation for the present invention, there is presented the following detailed examples. There examples, however, are presented for purposes of illustration only and are not to be considered as limiting the invention in any way.

EXAMPLE 1

1-Methyl Pyridinium Chloride

Chloromethane was liquified in a cold trap using a dry ice-acetone bath. Up to four moles of the liquified alkyl halide was directly added to the pre-cooled inner glass container of a Parr 4521 pressure reaction apparatus containing 10% stoichiometric excess chilled pyridine. The mixture was sealed in the pressure reaction apparatus and allowed to stand for approximately 2 days at room temperature. The resulting white, hygroscopic crystals were washed three times with anhydrous ether, suction filtered, and dried at 34° C. in a vacuum oven. The crystals were then stored under a high purity drybox nitrogen atmosphere. This procedure gave a 46% yield of crystals, mp 146°–148° C., (lit. mp 149° C.). NMR, $\delta 4.87$ (s, 3 protons), $\delta 8.23$ (t, 2 protons), $\delta 8.70$ (t, 1 proton), $\delta 9.77$ (d, 2 protons).

EXAMPLE 2

1-Ethyl Pyridinium Chloride

Liquified chloroethane was mixed with 10% excess chilled pyridine, sealed in the Parr pressure reaction apparatus and heated for 3 hrs. at 120° C. The resulting white, extremely hygroscopic crystals were washed three times with anhydrous ether and dried. This procedure gave a 83.4% yield of crystals, mp 116°–118° C., (lit, mp 118°–120° C.). NMR, $\delta 1.75$ (t, 3 protons), $\delta 5.18$ (q, 2 protons), $\delta 8.20$ (t, 2 protons), $\delta 8.60$ (t, 1 proton), $\delta 9.90$ (d, 2 protons).

EXAMPLE 3

1-Propyl Pyridinium Chloride 1-Chloropropane and 10% excess pyridine were mixed, sealed in the Parr apparatus and heated for 5 hours at 110° C. The resulting white, slightly hygroscopic crystals were washed with anhydrous ether and dried. This procedure gave a 71% yield of crystals, mp 92.5°–94.0° C. NMR, 1.03 (t, 3 protons), 2.12 (m, 2 protons), 5.10 (t, 2 protons), 8.23 (t, 2 protons), 8.65 (t, 1 proton), 9.90 (d, 2 protons).

EXAMPLE 4

1-Butyl Pyridinium Chloride

1-Chlorobutane and 10% excess pyridine were refluxed for 6 hrs. and gave a 63% yield of white, slightly hygroscopic crystals, mp 130°–141° C. NMR, 0.75 (t, 3 protons), 1.47 (m, 2 protons), 213 (p, 2 protons), 5.13 (t, 2 protons), 8.25 (t, 2 protons), 8.65 (t, 1 proton), 9.92 (d, 2 protons).

The NMR spectra were run in CDCl$_3$ (Me$_4$Si) on a Varian T-60A spectrometer. Uncorrected melting points were measured in sealed capillary tubes using a Mel-Temp apparatus. Hygroscopic chemicals were handled in a Vacuum/Atmospheres Co. glove box (model HE43-6 DRI-LAB) with a moisture content maintained below 10 ppm.

The pyridine (Baker) reagent grade, was dried using CaH$_2$, distilled and stored over 4 Å molecular sieves. Chloromethane (Union Carbide), chloroethane (Union Carbide), 1-chloropropane (Aldrich) and 1-chlorobutane (Eastman) were used without further purification.

What is claimed is:

1. A method for synthesizing 1-alkyl pyridinium chloride which comprises the steps of (1) effecting a reaction within a closed reaction vessel between (A) a liquified alkyl chloride selected from the group consisting of methyl chloride, ethyl chloride, 1-propyl chloride and 1-butyl chloride wherein said alkyl chloride was previously liquified in a cold trap of acetone and (B) 10 percent stoichiometric excess pyridine; (2) continuing said reaction under pressure at a temperature of from room temperature to about 120° C. and for a period of time sufficient to produce said alkyl pyridinium chloride; and (3) washing the product of step (2) in ether, followed by filtering and vacuum drying.

2. A method in accordance with claim 1 wherein said alkyl chloride is methyl chloride.

3. A method in accordance with claim 1 wherein said alkyl chloride is ethyl chloride.

4. A method in accordance with claim 1 wherein said alkyl chloride is 1-propyl chloride.

5. A method in accordance with claim 1 wherein said alkyl chloride is 1-butyl chloride.